(12) United States Patent  
Mordehai et al.

(10) Patent No.: US 9,281,173 B2  
(45) Date of Patent: Mar. 8, 2016

(54) ION PROCESSING UTILIZING SEGMENTED VACUUM MANIFOLD

(71) Applicant: Agilent Technologies, Inc., Loveland, CO (US)

(72) Inventors: Alexander Mordehai, Loveland, CO (US); Mark H. Werlich, Loveland, CO (US); Ruwan T. Kurulugama, Loveland, CO (US); Thomas A. Knotts, Loveland, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 13/906,023

(22) Filed: May 30, 2013

(65) Prior Publication Data

US 2014/0353483 A1 Dec. 4, 2014

(51) Int. Cl.
| | |
|---|---|
| *H01J 49/06* | (2006.01) |
| *H01J 49/26* | (2006.01) |
| *G01N 27/62* | (2006.01) |

(52) U.S. Cl.
CPC ............ *H01J 49/062* (2013.01); *G01N 27/622* (2013.01); *H01J 49/26* (2013.01)

(58) Field of Classification Search
CPC .......... H01J 49/24; H01J 49/424; H01J 49/49
USPC ....................................................... 250/281
See application file for complete search history.

(56) References Cited

U.S. PATENT DOCUMENTS

| | | | |
|---|---|---|---|
| 5,235,182 A | 8/1993 | Avida et al. | |
| 6,469,295 B1 * | 10/2002 | Park | 250/282 |
| 6,639,213 B2 | 10/2003 | Gillig et al. | |
| 6,762,404 B2 * | 7/2004 | Bateman et al. | 250/281 |
| 6,809,313 B1 * | 10/2004 | Gresham et al. | 250/287 |
| 7,155,812 B1 * | 1/2007 | Peterson et al. | 29/610.1 |
| 7,838,821 B2 | 11/2010 | Clemmer et al. | |
| 7,858,926 B1 * | 12/2010 | Whitehouse et al. | 250/281 |
| 2007/0114382 A1 * | 5/2007 | Clemmer et al. | 250/287 |
| 2007/0278396 A1 * | 12/2007 | Wu | 250/282 |
| 2011/0057097 A1 * | 3/2011 | Bateman et al. | 250/283 |
| 2012/0153140 A1 * | 6/2012 | Makarov | 250/282 |
| 2013/0009053 A1 | 1/2013 | Wu | |

* cited by examiner

*Primary Examiner* — David A Vanore  
*Assistant Examiner* — Kevin Chung

(57) ABSTRACT

An ion processing device includes electrically conductive vacuum manifold segments serially positioned and enclosing a volume along an axis. The segments are electrically isolated from each other and independently addressable by a voltage source. An ion optics device is positioned in the volume. A voltage differential between each manifold segment and the ion optics device is maintained below a maximum value by applying different voltages to respective manifold segments. The voltage differential may be controlled to avoid voltage breakdown in a low-pressure, high-voltage gas environment. The ion optics device may in some cases be an ion mobility drift cell.

20 Claims, 4 Drawing Sheets

ION PROCESSING UTILIZING SEGMENTED VACUUM MANIFOLD

TECHNICAL FIELD

The present invention relates to ion processing devices utilized in spectrometry, such as mass spectrometry and ion mobility spectrometry, and more particularly to vacuum manifolds provided with ion processing devices.

BACKGROUND

A spectrometry system in general includes an ion source for ionizing components of a sample of interest, an analyzer for separating the ions based on a discriminating attribute, an ion detector for counting the separated ions, and electronics for processing output signals from the ion detector as needed to produce user-interpretable spectral information. In a mass spectrometry (MS) system, the analyzer is a mass analyzer that separates the ions based on their differing mass-to-charge ratios (or m/z ratios, or more simply "masses"). Depending on design, the mass analyzer may separate ions by utilizing electric and/or magnetic fields, or time-of-flight tubes. The mass analyzer is maintained at low vacuum in a manifold (or housing, chamber, etc.). In an ion mobility spectrometry (IMS) system, the analyzer is a drift cell that separates ions based on their different cross-sectional areas. The drift cell is enclosed in a manifold that in some IM techniques may be maintained a vacuum level in the range of, for example, 1 to 5 Torr. IM separation occurs as ions travel a known distance through a known environment of drift gas at a known pressure, which may be a vacuum level in the range of, for example, 1 to 5 Torr. Ions of differing cross-sectional areas have differing mobilities through the gas environment. Ions are pulled through the drift cell by a DC voltage gradient. Typical electric fields utilized in a low-field IMS technique range from, for example, 10 to 20 V/cm. An IMS may be coupled with an MS to provide unique two-dimensional information about an analyte under investigation. All such systems may further include other types of ion processing devices (e.g., ion guides) that include ion optics enclosed in vacuum stages and operating at high voltages.

Working with high voltages in a vacuum in the range of 1 to 10 Torr can be particularly challenging due to the increased susceptibility of voltage breakdown, which can adversely affect the operation of an ion processing or analyzing device. This is a well-known phenomenon described by the equations of the Paschen Curve for various gases (e.g., hydrogen, helium, nitrogen, noble gases). Generally, the breakdown voltage required to cause an electrical discharge or arc between two electrodes is a function of gas pressure and the spacing (gap distance) between the electrodes. Prior solutions for overcoming the problem of voltage breakdown include enclosing the high voltage elements in an insulating structure inside a metal vacuum manifold, or increasing the spacing between the high voltage elements and the vacuum manifold, or constructing the vacuum manifold from insulating materials. The prior solutions result in increased cost and large, bulky, and often unreliable vacuum manifold structures.

Therefore, there remains an ongoing need for ion processing devices and systems utilizing vacuum manifolds configured and/or operated to better address the problem of voltage breakdown.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, an ion processing device includes: a vacuum manifold comprising a plurality of electrically conductive manifold segments serially positioned and enclosing a volume along an axis, the manifold segments electrically isolated from each other wherein each manifold segment is independently addressable by a voltage source; and an ion optics device positioned in the volume along the axis and comprising an ion entrance and an ion exit, the ion optics device configured for applying an axial voltage gradient from the ion entrance to the ion exit.

According to another embodiment, a spectrometry system includes: the ion processing device; and an ion detector communicating with the ion exit.

According to another embodiment, a method for processing ions includes: establishing a vacuum in a volume enclosed by a plurality of manifold segments serially positioned along an axis; introducing ions into an ion entrance of an ion optics device positioned in the volume; applying an axial voltage gradient to the ion optics device to transport the ions along the axis toward an ion exit of the ion optics device; and maintaining a voltage differential between each manifold segment and the ion optics device below a maximum value, the voltage differential being oriented in a direction orthogonal to the axis, by applying different voltages to respective manifold segments.

According to another embodiment, an ion processing device or spectrometry system is configured for performing any of the methods disclosed herein.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1:
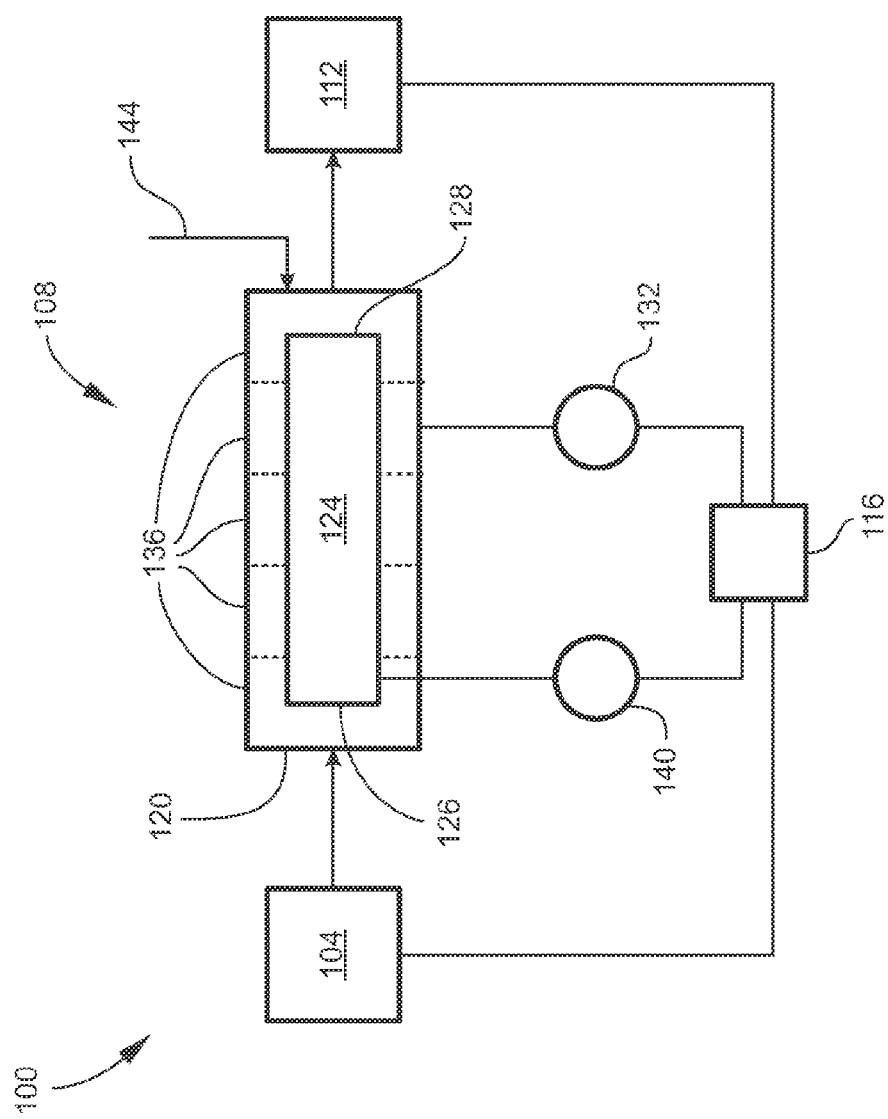
FIG. 1 is a schematic view of an example of a spectrometry system according to some embodiments.

FIG. 1 is a schematic view of an example of a spectrometry system 100 according to some embodiments. The spectrometry system 100 generally includes an ion source 104, one or more ion processing devices 108, an ion detector 112, and a system controller 116. The spectrometry system 100 may be any type of spectrometry system such, for example, an ion mobility spectrometry (IMS) system, a mass spectrometry (MS) system, or a hybrid system such as an IMS-MS system. The operation and design of specific components of such systems are generally known to persons skilled in the art and thus need not be described in detail herein. Instead, certain components are briefly described herein to facilitate an understanding of the subject matter presently disclosed.

The ion source 104 may be any type of continuous-beam or pulsed ion source suitable for producing analyte ions for spectrometry. Examples of ion sources 104 include, but are not limited to, electrospray ionization (ESI) sources, other atmospheric pressure ionization (API) sources, photo-ionization (PI) sources, electron ionization (EI) sources, chemical ionization (CI) sources, field ionization (FI) sources, plasma or corona discharge sources, laser desorption ionization (LDI) sources, and matrix-assisted laser desorption ionization (MALDI) sources. In some embodiments, the ion source 104 may include two or more ionization devices, which may be of the same type or different type. Depending on the type of ionization implemented, the ion source 104 may reside in a vacuum chamber or may operate at or near atmospheric pressure. Sample material to be analyzed may be introduced to the ion source 104 by any suitable means, including hyphenated techniques in which the sample material is the output of an analytical separation instrument such as, for example, a gas chromatography (GC) or liquid chromatography (LC) instrument (not shown).

The ion processing device 108 includes a vacuum manifold 120 (or vacuum manifold assembly) and an ion optics device 124 positioned in the vacuum manifold 120. The ion optics device 124 generally includes an ion inlet 126, and ion outlet 128, and one or more electrodes addressable by a voltage source 132 (i.e., one or more sources of electrical power and associated electronics). The ion optics device 124 may be any type of device for guiding ions along a linear (straight or curved) ion path. Depending on the design and function of the ion optics device 124, RF and/or DC voltage potentials may be applied to the electrode(s) of the ion optics device 124, such as for accelerating and/or focusing ions. As described further by example below, the vacuum manifold 120 has a segmented configuration. That is, the vacuum manifold 120 includes a plurality of manifold segments 136 arranged in series along the longitudinal axis of the ion processing device 108. The manifold segments 136 collectively enclose a manifold interior (or volume) having a length along the axis. The manifold segments 136 are constructed (in whole or part) of electrically conductive materials, and adjacent manifold segments 136 are electrically isolated from each other by appropriately structured insulating members (not shown). By this configuration, each manifold segment 136 may be independently energized at a desired voltage. A single voltage source 140 in FIG. 1 schematically represents hardware utilized to apply voltages to respective manifold segments 136. Individual voltages may be selectively applied to individual manifold segments 136 to control the electric field conditions surrounding the ion optics device 128 in the interior of the vacuum manifold 120. In some embodiments, each manifold segment 136 includes a non-conductive surface coating on the conductive portion for electrical isolation. The ion processing device 108 may also include a gas conduit 144 for establishing a flow of gas into the interior, for example an inert drift gas (e.g., nitrogen, argon, etc.), such as in a case where the ion optics device 128 is configured as an ion mobility drift cell.

In some embodiments, the ion processing device 108 schematically represents one or more other ion processing components that may be included between the ion source 104 and the ion detector 112 in accordance with the particular design of the spectrometry system 100, the type of sample to be analyzed, and the type of experiments to be conducted. Examples of other ion processing components may include, but are not limited to, an interface with the ion source 104 for receiving ions therefrom, a mass filter, an ion trap, a collision cell, an ion guide, various types of ion optics for focusing the ion beam and controlling the transport and energy of ions, an interface for transmitting ions to the ion detector 112, etc. Pressure in these other ion processing components may be controlled by one or more different vacuum stages.

The ion detector 112 may be any device configured for collecting and measuring the flux (or current) of ions outputted from the ion processing device 108. Examples of ion detectors 112 include, but are not limited to, electron multipliers, photomultipliers, and Faraday cups. In some embodiments, the ion detector 112 may be (or be part of) an analytical device such as an MS.

Figure 2:
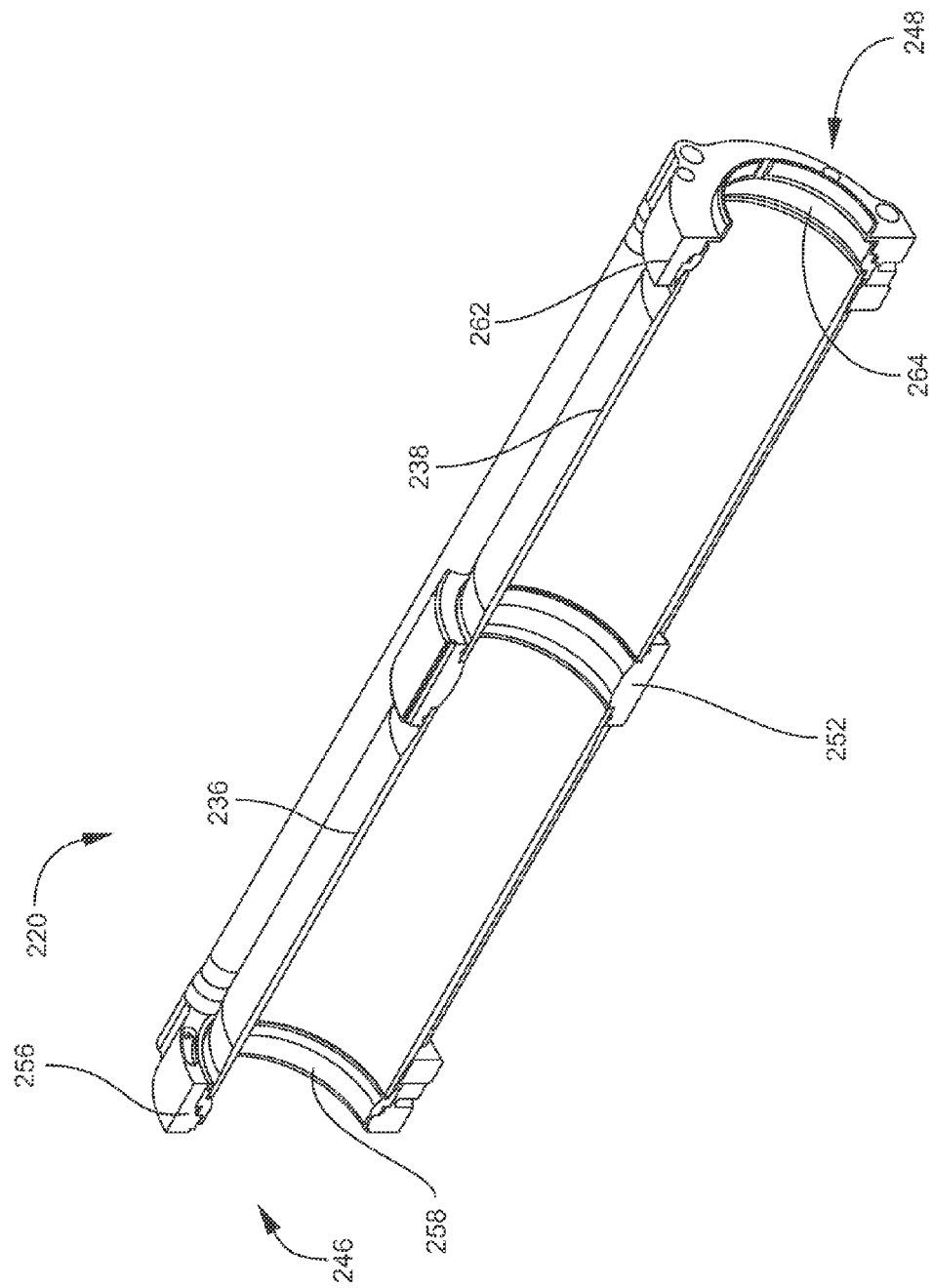
FIG. 2 is a perspective cut-away view of an example of a vacuum manifold according to some embodiments.

FIG. 2 is a perspective cut-away view of an example of a vacuum manifold 220 according to some embodiments. The vacuum manifold includes a plurality of electrically conductive manifold segments positioned in series along an axis and collectively enclosing a manifold interior having a manifold entrance 246 and a manifold exit 248. In a typical embodiment the manifold segments are cylindrical, although more generally they are not limited to any particular geometry. Two manifold segments are shown by example in FIG. 2. More generally, the vacuum manifold 220 may include any number of manifold segments, e.g., a front manifold segment 236 at the entrance 246, one or more intermediate manifold segments (not shown), and a rear manifold segment 238 at the exit 248. Each manifold segment is isolated from an adjacent manifold segment by an insulating member 252, which may generally be ring-shaped in accordance with the geometry illustrated by example in FIG. 2. The vacuum manifold 220 may include a front manifold electrode 256 at (directly at, or proximate to) the entrance 246, which may be isolated from the front manifold segment 236 by an insulating member 258. The vacuum manifold 220 may also include a rear manifold electrode 262 at (directly at, or proximate to) the exit 248, which may be isolated from the rear manifold segment 238 by an insulating member 264. The front manifold electrode 256 and rear manifold electrode 262 may be placed in signal communication with a voltage source. As noted above, the segmented configuration enables the manifold segments to be held at independent voltages.

Figure 3:
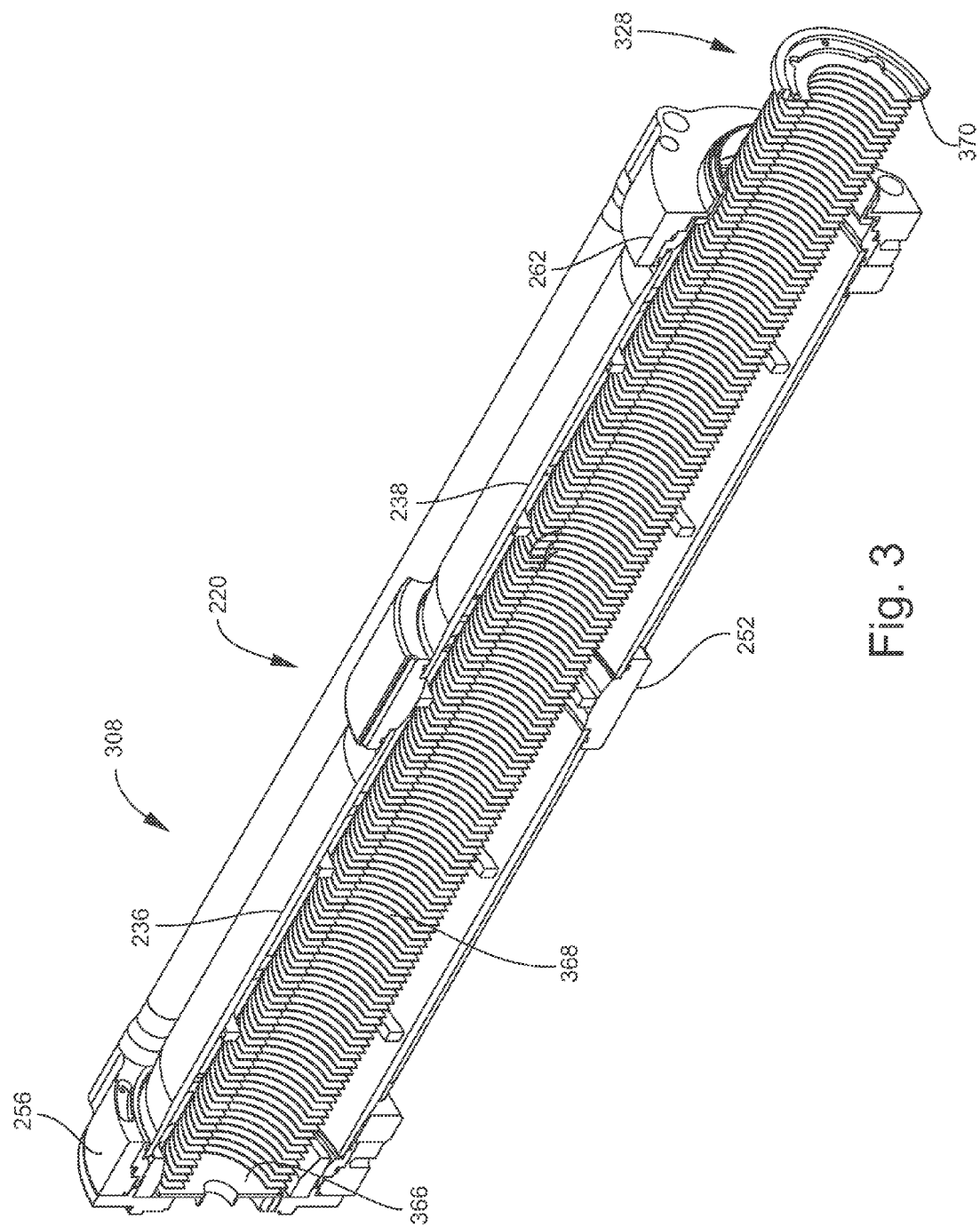
FIG. 3 is a perspective cut-away view of an example of an ion processing device according to some embodiments.

FIG. 3 is a perspective cut-away view of an example of an ion processing device 308 according to some embodiments. The ion processing device 308 includes an ion optics device 328 enclosed in the segmented vacuum manifold 220 described above and illustrated in FIG. 2. In the present embodiment, the ion optics device 328 includes a plurality of ring-shaped lens elements positioned in series along the axis of the ion processing device 308, including a front lens element 366, several intermediate lens elements 368, and a rear lens element 370. FIG. 3 shows the rear portion of the ion optics device 328 extending beyond the rear manifold electrode 262. In this example, an additional manifold segment (not shown) held at ground potential may surround the rear portion and serve as a transition to a downstream device (e.g., an ion guide or the like).

In some embodiments, the ion processing device 308 may be configured as an IMS instrument. Ion packets may be introduced through the front lens element 366 of the ion optics device 328, which operates as a drift cell in this example. The ion optics device 328 generates an axial DC voltage gradient along its length to move ions through the ion optics device 328 against a drift gas, whereby the ions become separated in time based on their different cross-sections as appreciated by persons skilled in the art. The DC voltage gradient may be generated in a known manner, such as by applying a voltage between the front lens element 366 and rear lens element 370 and through a resistive divider network such that successively lower voltages are applied to successive lens elements along the length of the ion optics device 328. The voltage gradient may be uniform, i.e., the voltage may vary along the length at a uniform rate. As one non-limiting example, the voltage on the front lens element 366 may be 1800 V and the voltage on the rear lens element 370 may be 300 V.

During operation, a radial voltage differential exists across the space between the ion optics device 328 and the surrounding vacuum manifold 220, i.e., in the radial direction orthogonal to the longitudinal axis of the ion processing device 308. To minimize the chance of voltage breakdown in the low vacuum environment of the ion processing device 308, a voltage ("manifold voltage") is applied to the vacuum manifold 220 that varies in the axial direction along the length of the vacuum manifold 220. This may be achieved by applying independent voltages to respective manifold segments 236 and 238 and manifold electrodes 256 and 262. Voltage breakdown is avoided by maintaining the radial voltage differential below a maximum value. The radial voltage differential may be kept below the maximum value over the entire length of the vacuum manifold 220 by selecting appropriate magnitudes for the voltages to be applied to the respective manifold segments 236 and 238 and manifold electrodes 256 and 262, relative to the magnitudes of the voltages being applied to the ion optics lens elements 366, 368 or 370 in the vicinity of a given manifold segment or manifold electrode. The voltage applied to the vacuum manifold 220 may essentially track the voltage applied to the ion optics device 328 along the axial direction. For example, voltages of successively reduced values may be applied to the front manifold electrode 256, the front manifold segment 236, the rear manifold segment 238, and the rear manifold electrode 262, respectively.

As the vacuum manifold 220 includes fewer electrically conductive components than the ion optics device 328, the radial voltage differential between the ion optics device 328 and vacuum manifold 220 may vary along the axial direction in a step-wise manner that is coarser than the DC voltage gradient impressed along the ion optics device 328. This, however, does not affect the ability to keep the voltage differential below a desired maximum value. Moreover, the tuning or resolution of the voltage "tracking" along the device axis may be made finer by, for example, adding more independently energized manifold segments that are shorter in axial length relative to the ion optics device 328.

The maximum value for the radial voltage differential may be determined based on a variety of factors, including the axial DC gradient applied to the ion optics device 328, the spacing between the ion optics device 328 and the vacuum manifold 220, the operating pressure, and the type of drift gas employed. In the present context, the "spacing" may refer to the radial distance between the inside surface of (or inside envelope occupied by) the vacuum manifold 220 and the outside surface of (or outside envelope occupied by) the ion optics device 328. As an example, in some embodiments the spacing may be in a range from 2 mm to 50 mm. In some embodiments the operating pressure may be in a range from 0.1 Torr to 760 Torr. In some embodiments, the maximum value for the radial voltage differential is in a range from about 50 V to 10,000 V.

Figure 4:
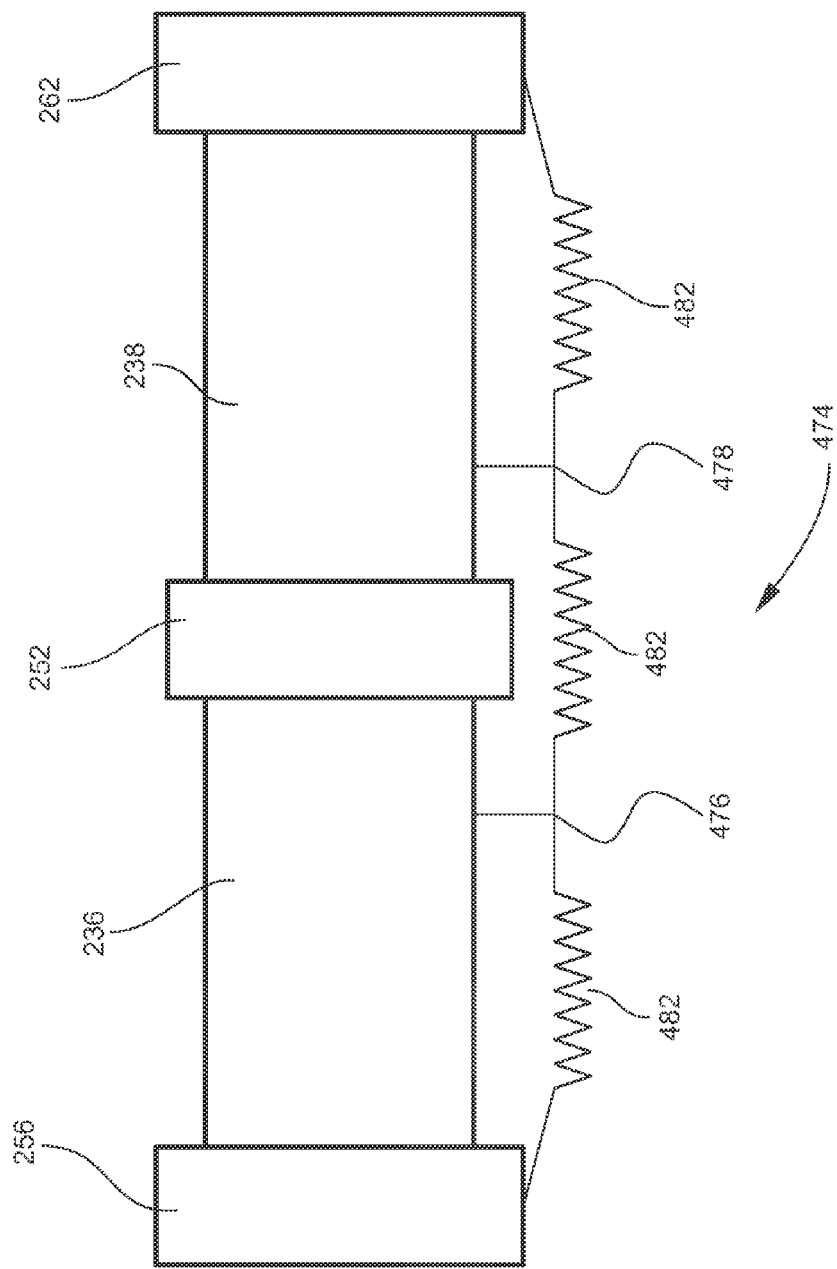
FIG. 4 is a schematic view of a vacuum manifold illustrating one example of applying independent voltages to different components.

FIG. 4 is a schematic view of the vacuum manifold 220 illustrating one example of applying independent voltages to different components. A voltage source is configured for applying the manifold voltage between the front electrode 256 and rear electrode 262. A voltage divider 474 is in signal communication with the front electrode 256 and rear electrode 262, with tap-off points 476 and 478 in signal communication with respective manifold segments 236 and 238. Resistors 482 arranged in series between adjacent components may represent various kinds of resistive components as appreciated by persons skilled in the art. The resistances of the resistors 482 may all be equal, or alternatively at least one resistance may be different from the other resistances. In the case of all equal resistances, the voltages (magnitudes) applied to the front manifold segment 236 and rear manifold segment 238 will be about 67% and about 33%, respectively, of the voltage applied to the front electrode 256. In this embodiment, the rear electrode 262 is connected to instrument ground.

As one non-limiting example, the voltage applied to the front electrode 256 is 1800 V and the rear electrode 262 is held at ground potential, resulting in a voltage applied to the front manifold segment 236 of about 1200 V and a voltage applied to the rear manifold segment 238 of about 600 V. With the DC gradient applied to the ion optics device 328 (FIG. 3) as given by example above, this configuration results in a maximum voltage differential of 600 V between the ion optics device 328 and the vacuum manifold 220 at any point along the length of the vacuum manifold 220.

From the foregoing, it may be seen that embodiments described herein enable the voltage differential between ion optics and a surrounding vacuum manifold to be controlled, and minimized if desired. Controlling the voltage differential so as not to exceed a maximum value is particularly useful for meeting voltage breakdown requirements, such as in the case of an IMS instrument. The reduced voltage differential may allow for a comparatively more compact design of the vacuum manifold due to reduced spacing requirements. It may also allow for a comparatively simpler, more cost-effective design by eliminating the requirement for surrounding the ion optics with insulating structures inside the vacuum manifold. Moreover, the segmented configuration of the vacuum manifold renders the design easily scalable, such as to accommodate higher voltages and/or longer ion optics. The size and number of manifold segments between entrance and exit may be selected to attain a desired degree of control of the voltage differential along the length of the device. In addition, the ion optics within the manifold will have substantially less electrical capacitance to ground compared to conventional manifolds. This is especially advantageous in cases where the voltages on the ion optical elements need to be switched in a timely manner.

EXEMPLARY EMBODIMENTS

Exemplary embodiments provided in accordance with the presently disclosed subject matter include, but are not limited to, the following:

1. An ion processing device, comprising: a vacuum manifold comprising a plurality of electrically conductive manifold segments serially positioned and enclosing a volume along an axis, the manifold segments electrically isolated from each other wherein each manifold segment is independently addressable by a voltage source; and an ion optics device positioned in the volume along the axis and comprising an ion entrance and an ion exit, the ion optics device configured for applying an axial voltage gradient from the ion entrance to the ion exit.

2. The ion processing device of embodiment 1, comprising a voltage source configured for applying respective voltages to different manifold segments.

3. The ion processing device of embodiment 2, wherein the voltage source is configured for maintaining a voltage differential between each manifold segment and the ion optics device below a maximum value, the voltage differential being oriented in a direction orthogonal to the axis.

4. The ion processing device of any of embodiments 1-3, comprising a voltage divider in signal communication with the manifold segments.

5. The ion processing device of embodiment 4, wherein the plurality of manifold segments comprises at least a front manifold segment and a rear manifold segment, and further comprising a front electrode electrically isolated from the front manifold segment and in signal communication with the voltage divider, and a rear electrode electrically isolated from the rear manifold segment and in signal communication with the voltage divider.

6. The ion processing device of embodiment 5, wherein the voltage divider comprises a plurality of resistances between adjacent manifold segments.

7. The ion processing device of embodiment 6, wherein the plurality of resistances comprises a front resistance between the front electrode and the front manifold segment and a rear resistance between the rear manifold segment and the rear electrode.

8. The ion processing device of embodiment 6, wherein the resistances are of equal value.

9. The ion processing device of any of embodiments 1-8, wherein each manifold segment comprises an inside surface, the ion optics device comprises an outside surface, and the distance between the inside surface and the outside surface along a direction orthogonal to the axis is in a range from 2 mm to 50 mm.

10. The ion processing device of any of embodiments 1-9, wherein each manifold segment comprises a non-conductive surface coating.

11. The ion processing device of any of embodiments 1-10, wherein the ion optics device comprises a plurality of lens elements serially positioned along the axis.

12. A spectrometry system, comprising: the ion processing device of any of embodiments 1-11; and an ion detector communicating with the ion exit.

13. The spectrometry system of embodiment 12, wherein the ion optics device is configured as an ion mobility drift cell.

14. The spectrometry system of embodiment 12 or 13, wherein the ion detector is a mass spectrometer.

15. The spectrometry system of any of embodiments 12-14, comprising a gas conduit communicating with the vacuum manifold.

16. A method for processing ions, the method comprising: establishing a vacuum in a volume enclosed by a plurality of manifold segments serially positioned along an axis; introducing ions into an ion entrance of an ion optics device positioned in the volume; applying an axial voltage gradient to the ion optics device to transport the ions along the axis toward an ion exit of the ion optics device; and maintaining a voltage differential between each manifold segment and the ion optics device below a maximum value, the voltage differential being oriented in a direction orthogonal to the axis, by applying different voltages to respective manifold segments.

17. The method of embodiment 16, comprising maintaining the vacuum in a range from 0.1 Torr to 760 Torr.

18. The method of embodiment 16 or 17, wherein applying the axial voltage gradient comprises applying voltages to a series of lenses of the ion optics device.

19. The method of any of embodiments 16-18, wherein the maximum value below which the voltage differential is maintained is in a range from 50 V to 10,000 V.

20. The method of any of embodiments 16-19, wherein applying different voltages comprises applying voltages of successively reduced values to the respective manifold segments.

21. The method of any of embodiments 16-20, wherein the plurality of manifold segments comprises at least a front manifold segment defining a manifold entrance and a rear manifold segment defining a manifold exit, and applying different voltages comprises applying a manifold voltage between a front electrode at the manifold entrance and a rear electrode at the manifold exit and through a voltage divider between the front electrode and the rear electrode, wherein different manifold segments are tapped into different points of the voltage divider.

22. The method of any of embodiments 16-21, comprising establishing a flow of gas into the volume wherein the ions in the ion optics device collide with the gas.

23. The method of any of embodiments 16-22, comprising transferring the ions from the ion optics device to a detector.

24. The method of embodiment 23, comprising operating the detector to discriminate among different types of the ions based on mobility, mass-to-charge ratio, or both mobility and mass-to-charge ratio.

The system controller 116 schematically depicted in FIG. 1 may represent one or more modules configured for controlling, monitoring and/or timing various functional aspects of the spectrometry system 100 such as, for example, the ion source 104, the voltage sources 132 and 140 of the ion processing device 108, the ion detector 112, gas flow control devices (not shown), and vacuum pumps. The system controller 116 may also be configured for receiving the ion detection signals from the ion detector 112 and performing tasks relating to data acquisition and signal analysis as necessary to generate spectral information characterizing the sample under analysis. The system controller 116 may include a computer-readable medium that includes instructions for performing any of the methods disclosed herein. For all such purposes, the system controller 116 is schematically illustrated as being in signal communication with various components of the spectrometry system 100 via wired or wireless communication links represented by lines. Also for these purposes, the system controller 116 may include one or more types of hardware, firmware and/or software, as well as one or more memories and databases. The system controller 116 typically includes a main electronic processor providing overall control, and may include one or more electronic processors configured for dedicated control operations or specific signal processing tasks. The system controller 116 may also schematically represent all voltage sources not specifically shown, as well as timing controllers, clocks, frequency/waveform generators and the like as needed for operating the spectrometry system 100. The system controller 116 may also be representative of one or more types of user interface devices, such as user input devices (e.g., keypad, touch screen, mouse, and the like), user output devices (e.g., display screen, printer, visual indicators or alerts, audible indicators or alerts, and the like), a graphical user interface (GUI) controlled by software, and devices for loading media readable by the electronic processor (e.g., logic instructions embodied in software, data, and the like). The system controller 116 may include an operating system (e.g., Microsoft Windows® software) for controlling and managing various functions of the system controller 116.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the system controller 116 schematically depicted in FIG. 1. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), or application specific integrated circuits (ASICs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the system controller 116 in FIG. 1), direct the electronic system to carry out the instructions. The computer program product may be selectively embodied in any non-transitory computer-readable storage medium for use by or in connection with an instruction execution system, apparatus, or device, such as an electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. An ion processing device, comprising:
    a vacuum manifold comprising a plurality of electrically conductive manifold segments serially positioned and enclosing a volume along a longitudinal axis, the manifold segments electrically isolated from each other wherein each manifold segment is independently addressable by a voltage source; and
    an ion optics device positioned in the volume along the longitudinal axis and spaced from the vacuum manifold along a radial direction orthogonal to the longitudinal axis, the ion optics device comprising an ion entrance and an ion exit and configured for applying an axial voltage gradient from the ion entrance to the ion exit.

2. The ion processing device of claim 1, comprising a voltage source configured for applying respective voltages to different manifold segments.

3. The ion processing device of claim 2, wherein the voltage source is configured for maintaining a voltage differential between each manifold segment and the ion optics device below a maximum value, the voltage differential being oriented in a direction orthogonal to the axis.

4. The ion processing device of claim 1, comprising a voltage divider in signal communication with the manifold segments.

5. The ion processing device of claim 4, wherein the plurality of manifold segments comprises at least a front manifold segment and a rear manifold segment, and further comprising a front electrode electrically isolated from the front manifold segment and in signal communication with the voltage divider, and a rear electrode electrically isolated from the rear manifold segment and in signal communication with the voltage divider.

6. The ion processing device of claim 5, wherein the voltage divider comprises a plurality of resistances between adjacent manifold segments.

7. The ion processing device of claim 6, wherein the plurality of resistances comprises a front resistance between the front electrode and the front manifold segment and a rear resistance between the rear manifold segment and the rear electrode.

8. The ion processing device of claim 6, wherein the resistances are of equal value.

9. The ion processing device of claim 1, wherein each manifold segment comprises an inside surface, the ion optics device comprises an outside surface, and the distance between the inside surface and the outside surface along a direction orthogonal to the axis is in a range from 2 mm to 50 mm.

10. The ion processing device of claim 1, wherein each manifold segment comprises a non-conductive surface coating.

11. The ion processing device of claim 1, wherein the ion optics device comprises a plurality of lens elements serially positioned along the axis.

12. A spectrometry system, comprising:
the ion processing device of claim 1; and
an ion detector communicating with the ion exit.

13. The spectrometry system of claim 12, wherein the ion optics device is configured as an ion mobility drift cell.

14. The spectrometry system of claim 12, comprising a gas conduit communicating with the vacuum manifold.

15. A method for processing ions, the method comprising:
establishing a vacuum in a volume enclosed by a plurality of manifold segments serially positioned along a longitudinal axis;
introducing ions into an ion entrance of an ion optics device positioned in the volume and spaced from the vacuum manifold along a radial direction orthogonal to the longitudinal axis;
applying an axial voltage gradient to the ion optics device to transport the ions along the longitudinal axis toward an ion exit of the ion optics device; and
maintaining a voltage differential between each manifold segment and the ion optics device below a maximum value, the voltage differential being oriented in the radial direction, by applying different voltages to respective manifold segments.

16. The method of claim 15, comprising maintaining the vacuum in a range from 0.1 Torr to 760 Torr.

17. The method of claim 15, wherein applying the axial voltage gradient comprises applying voltages to a series of lenses of the ion optics device.

18. The method of claim 15, wherein the maximum value below which the voltage differential is maintained is in a range from 50 V to 10,000 V.

19. The method of claim 15, wherein applying different voltages comprises applying voltages of successively reduced values to the respective manifold segments.

20. The method of claim 15, wherein the plurality of manifold segments comprises at least a front manifold segment defining a manifold entrance and a rear manifold segment defining a manifold exit, and applying different voltages comprises applying a manifold voltage between a front electrode at the manifold entrance and a rear electrode at the manifold exit and through a voltage divider between the front electrode and the rear electrode, wherein different manifold segments are tapped into different points of the voltage divider.

* * * * *